United States Patent [19]

Gray

[11] Patent Number: 4,928,685

[45] Date of Patent: May 29, 1990

[54] CLOSED-CIRCUIT POSITIVE PRESSURE BREATHING APPARATUS WITH PNEUMATICALLY OPERATED STORAGE CHAMBER

[75] Inventor: Robert E. Gray, Glen Mills, Pa.

[73] Assignee: Cairns & Brother Inc., Clifton, N.J.

[21] Appl. No.: 253,710

[22] Filed: Oct. 5, 1988

[51] Int. Cl.[5] .............................................. A61M 16/00

[52] U.S. Cl. .......................... 128/204.24; 128/205.12; 128/205.14; 128/205.24

[58] Field of Search ...................... 128/204.24, 205.12, 128/205.14, 205.28, 205.13, 205.24

[56] References Cited

U.S. PATENT DOCUMENTS

| | | | |
|---|---|---|---|
| 3,046,979 | 7/1962 | Andreasen | 128/204.28 |
| 3,058,460 | 10/1962 | Goodner | 128/205.13 |
| 3,126,001 | 3/1964 | Engström | 128/205.13 |
| 3,251,359 | 5/1966 | Ismach | 128/205.24 |
| 3,339,545 | 9/1967 | Burchell | 128/205.14 |
| 3,695,263 | 10/1972 | Kipling | 128/204.24 |
| 3,981,301 | 9/1976 | Warnow et al. | 128/204.24 |
| 4,069,818 | 1/1978 | Schreiber | 128/204.24 |
| 4,364,384 | 12/1982 | Warncke et al. | 128/205.12 |

*Primary Examiner*—Edgar S. Burr
*Assistant Examiner*—Aaron J. Lewis
*Attorney, Agent, or Firm*—Louis E. Marn

[57] ABSTRACT

There is disclosed a self-contained breathing apparatus of the positive pressure type wherein there is provided a pneumatic servo mechanism responsive to a pressure sensor to drive a breathing storage chamber by expansion of an oxygen containing gas from a storage tank therefor.

9 Claims, 2 Drawing Sheets

CLOSED-CIRCUIT POSITIVE PRESSURE BREATHING APPARATUS WITH PNEUMATICALLY OPERATED STORAGE CHAMBER

BACKGROUND OF THE INVENTION (1) Field of the Invention

This invention relates to a self-contained breathing apparatus, and more particularly to a closed-circuit positive pressure self-contained breathing apparatus for temporary use by a wearer in a noxious environment, such as is worn by a firefighter. (2) Description of the Prior Art Self-contained breathing apparatus (SCBA's) are worn by industrial workers, and in particular firefighters, to provide a safe, respirable breathing condition while the user works in a hostile environment. Currently, breathing performance and service life rating of such apparatus are based upon user consumption at the rate of 40 liters per minute, wherein inhalation and exhalation reach peaks instantaneous flow rates of about 115 liters per minute. For firefighting duty, the National Fire Prevention Administration (NFPA) has defined new performance standards (for open circuit SCBA's) wherein peak instantaneous breathing rates exceed 200 liters per minute.

SCBA's are classified as open-circuit (where the user's exhalation is dumped from the system) or closed-circuit (where exhalation is returned to the system for subsequent reuse after carbon dioxide is removed and oxygen is added).

Although closed-circuit, self-contained breathing apparatus have existed longer than open-circuit types, there are some inherent disadvantages of closed-circuit systems which offset the substantial weight and size advantage they offer for extended duration. One disadvantage is the sluggish response of the system to the user's breathing requirements, particularly at high metabolic work rates. A second disadvantage is the design difficulty encountered in trying to create a constant positive pressure in the facepiece (positive pressure substantially increases the degree of respiratory protection to the wearer).

OBJECTS OF THE INVENTION

An object of the present invention is to provide an improved self-contained closed-circuit positive pressure breathing apparatus of extended rating which provides an amplified response to the user's breathing effort, resulting in very low breathing resistance.

Another object of the present invention is to provide an improved closed-circuit self-contained breathing apparatus which is capable of maintaining a positive pressure in the facepiece, even during high inhalation flow rates, but without having substantial resistance to high exhalation flows.

Still another object of the present invention is to provide an improved closed-circuit positive pressure self-contained breathing apparatus with breathing performance which meets or exceeds that of an open-circuit apparatus.

Yet another object of the present invention is to provide an improved closed-circuit self-contained positive pressure breathing apparatus.

SUMMARY OF THE INVENTION

These and other objects of the present invention are achieved in a self-contained breathing apparatus of the positive pressure type wherein there is provided a pneumatic servo mechanism responsive to a pressure sensor to drive a breathing storage chamber by expansion of an oxygen containing gas from a storage tank therefor.

BRIEF DESCRIPTION OF THE DRAWING

Further objects and advantages of the present invention will become apparent from the following detailed description thereof when taken with the accompanying drawings wherein like numerals designate like parts throughout, and wherein.

DETAILED DESCRIPTION OF THE INVENTION

Figure 1:
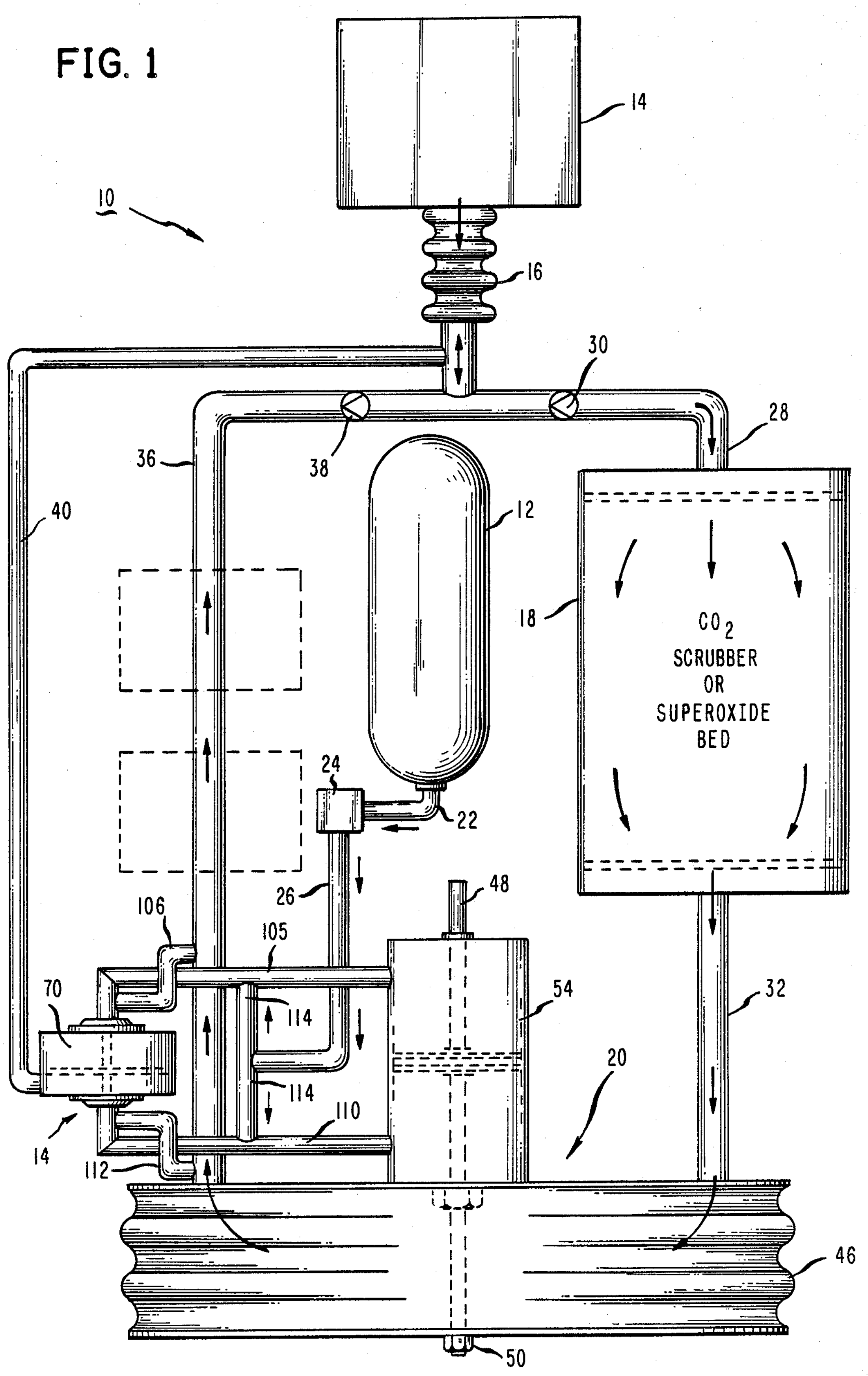
FIG. 1 is a schematic flow diagram of the positive pressure self-contained breathing apparatus of the present invention.

Referring now to FIG. 1, there is schematically illustrated a self-contained breathing apparatus of the present invention, generally indicated as 10, mounted in a supporting carrier assembly (not shown) including a helmet (H) and comprised of a compressed breathing gas supply tank 12; a pneumatic servovalve assembly, generally indicated as 14; an inhale/exhale delivery conduit 16; a canister assembly 18 and a breathing storage assembly 20. The breathing gas supply tank 12 (containing either air, oxygen, oxygen enriched air, or another mixture of oxygen in combination with other breathable gases) is of a size to provide about 2 to 5 liters of air to the system, depending on the user's metabolic work rate and is connected by a conduit 22 under the control of a pressure reducer valve 24 via a conduit 26 to the pneumatic servovalve assembly 14.

The inhale/exhale delivery conduit 16 is connected by a conduit 28 under the control of one-way valve 30 to the chemical canister assembly 18 for the removal of carbon dioxide (and possibly chemical addition of oxygen) therein as known to one skilled in the art. The canister assembly 18 is connected by a conduit 32 to the breathing storage assembly 20 defining a variable volume gaseous storage chamber 34 in fluid communication by a conduit 36 under the control of one-way valve 38 with the inhale/exhale delivery conduit 16. A conduit 40 is provided between the pneumatic servovalve assembly 14 and the inhale/exhale delivery conduit 16 to sense the breathing circuit pressure therein.

The canister assembly 18 contains a chemical bed (or beds) of one or more well known carbon dioxide-adsorbing material, and possibly one or more oxygen producing chemicals. Various carbon dioxide-adsorbing materials are well known and readily available at relatively inexpensive prices. The material producing oxygen could be one of several known chemicals which react with moisture and carbon dioxide to generate oxygen, such as potassium superoxide, lithium superperborate or the like.

Figure 2:
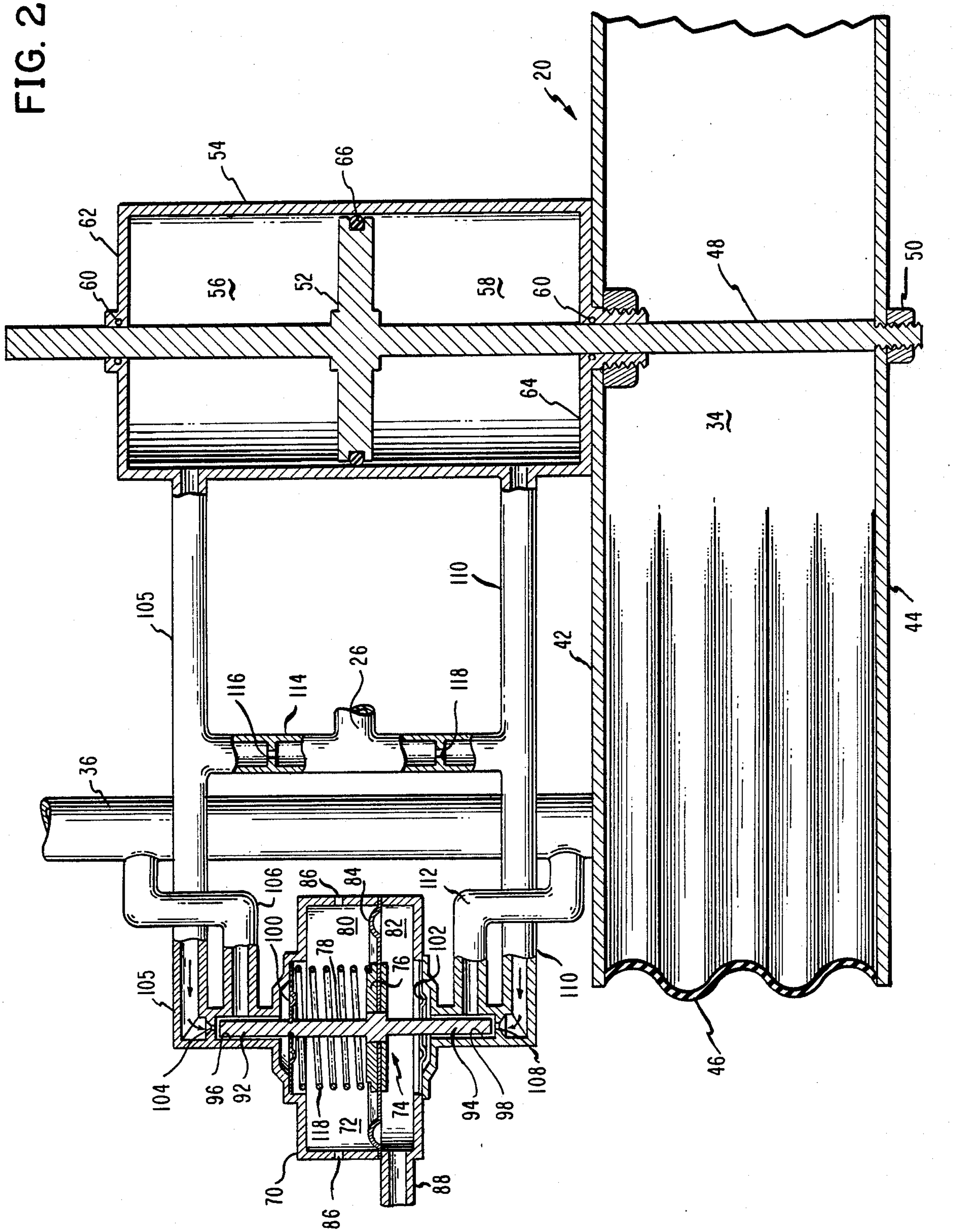
FIG. 2 is an enlarged partial cross-sectional plan view of the pressure regulating assembly.

The breathing storage assembly 20 is comprised of an upper wall 42 and a lower wall 44 connected by flexible bellowed-shaped side wall 46 and reinforced to withstand significant positive and negative internal pressure. Through the upper wall 42, referring particularly to FIG. 2, there is slidably positioned a rod member 48 vertically disposed for reciprocal movement and mounted by a nut 50 to the lower wall 44 of the breathing storage assembly 20. The rod member 48 is provided with a piston 52 disposed in a cylinder member 54 mounted to an upper surface portion of the upper wall 42 of the breathing storage chamber 34 and defining an upper chamber 56 and a lower chamber 58 therein.

The cylinder member 54 is preferably mounted to the upper wall 42 of the breathing storage assembly 20 to ensure positive displacement of the rod member 48 mounted to the lower wall member 44 with respect to the movement of the rod member 48 and associated piston 52 disposed within the cylinder member 54 as more fully hereinafter described. The rod member 48 is provided with appropriate sealing assemblies, such as ring members 60 disposed in upper and lower walls 62 and 64 of the cylinder member 54. The piston 52 is provided with a ring seal 66 to prevent fluid flow between the upper and lower chamber 56 and 58 of the cylinder member 54.

The pneumatic servovalve assembly 14 includes a cylindrically-shaped pressure sensor housing 70 defining a chamber 72 and having a diaphragm member, generally indicated as 74, including a disc-shaped body portion 76 and a spindle member 78 positioned within the chamber 72 and defining an upper chamber 80 and a lower chamber 82 with a donut-shaped flexible membrane member 84 attached between the body portion 76 and the pressure sensor housing 70. The upper portion of the pressure sensor housing 70 is provided with channels 86 to provide fluid communication between the atmosphere and the upper chamber 72 of the pressure sensor housing 70. A channel 88 is provided in the lower portion of the pressure sensor housing 70 to provide fluid communication between the lower chamber 82 and the conduit 40 as more fully hereinafter described.

The spindle member 78 is provided with an upper valve portion 92 and a lower valve portion 94 for positioning within valve seating chambers 96 and 98, respectively, formed in the upper and lower wall portions of the pressure sensor housing 70. Diaphragm seals 100 and 102 are mounted to the upper and lower portions of the spindle member 78 and to proximate portions of the pressure sensor housing 70 to isolate the chambers 80 and 82 from the valve seating chambers 96 and 98. The upper valve seating chamber 96 is in fluid communication via an orifice 104 with the chamber 56 of the member 54 by a conduit member 105 and with the conduit 36 via a conduit 106. The lower valve seating chamber 98 is in fluid communication via an orifice 108 with the chamber 58 of the cylinder member 54 via a conduit member 110 and with the conduit 36 via a conduit 112.

A positive pressure of approximately 20 mm. of water in the breathing conduit 16 is transmitted to the chamber 82 via the conduit 40 so that the spindle member 78 is lifted to a neutral position with equal flow restriction through orifices 104 and 108. An intermediate conduit 114 including reducing orifices 116 and 118 is provided for fluid communication between the conduit member 105 and the conduit member 110 and the conduit 26 to provide fluid communication of the compressed air from the pressure reducer 24 to the pneumatic servovalve assembly 14.

A coil spring 118 is provided in the upper chamber of the pressure sensor housing 70 to bias the valve portion 94 of the spindle member 78 against the needle valve chamber 98 in order to create a positive pressure in the breathing circuit. A positive pressure of approximately 20 mm. of water in the breathing conduit 16 is transmitted to the chamber 82 via the conduit 40 so that the spindle member 78 is lifted to a neutral position with equal flow restriction through orifices 104 and 108.

In operation, the spindle member 78 acts a rod stem at each end by restricting flow through either the upper orifice 104 or the lower orifice 108 thereby creating an imbalance in the pneumatic network comprised by the pneumatic resistance of the orifices 104, 108, 116 and 118. Thus, the chambers 56 and 58 of the cylinder member 54 function to control the movement of the piston 52 (and thus the movement of the breathing storage chamber 20) as a result of the pressure imbalance between the chambers 56 and 58.

During inhalation, the pressure on the breathing circuit in conduit 16 drops slightly below the 20 mm. static pressure, causing the pressure in the lower chamber 58 of the cylinder 54 to increase thereby applying a net upward force against the piston 52 of the rod member 48 to cause the lower wall 44 to rise and compress the breathing storage chamber 34 with sufficient force to overcome what ever resistance is present between the storage chamber 34 and the helmet (H). As the storage chamber 34 responds, pressure in the breathing circuit increases towards the 20 mm. static pressure thereby providing feed-back to the pneumatic servovalve assembly 14 thereby returning to a neutral position the spindle member 78 of the pressure sensor housing 70.

Similarly, exhalation causes an increase in breathing circuit pressure in conduit 16 which causes an increase in pressure in the upper chamber 56 of the cylinder member 54 causing the breathing storage chamber 34 to expand to assist overcoming resistance in the exhalation circuitry.

In accordance with the present invention, use is made of the energy in the pressurized breathing gas tank 12 to drive a servo assembly in response to the user's demand, energy otherwise unused, and without requiring substantially more gas than would be required to replenish oxygen or flush the rebreather system. Following its use in pneumatically amplifying the breathing response and driving the breathing storage chamber, the breathing gas is vented into the breathing circuit conduit 36 via conduits 106 and 112. In summary, the user's breathing creates a pressure change in the breathing conduit 16 which is transmitted through the conduit 40 to the lower chamber 82 of the pneumatic servovalve assembly 14 causing the spindle member 78 to respond up or down to restrict flow through either of the restrictive orifices 104 or 108, respectively.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed:

1. A rebreathing apparatus for use by a wearer having a respiratory system, which comprises:

an inhale/exhale breathing conduit;

an exhaust gas scrubber means for removing carbon dioxide from an exhaled gaseous stream and having an inlet connected to said inhale/exhale breathing conduit;

a breathing storage chamber including means for varying volume of said breathing storage chamber;

a conduit means for providing fluid flow between said exhaust gas scrubber means and said breathing storage chamber;

a conduit means for providing fluid flow between said breathing storage chamber and said inhale/exhale breathing conduit;

a breathing gas supply tank;

a pressure reducer valve having an inlet and an outlet;

a conduit means for providing fluid flow between said breathing gas supply tank and said inlet of said pressure reducer valve;

a pressure sensor means having a housing in fluid flow communication with said outlet of said pressure reducer valve, said pressure sensor means having a piston defining at least two fluidically separate chambers within said housing, one of said chambers being in constant fluid communication with ambient pressure and the other of said chambers being in fluid communication with said inhale/exhale breathing conduit, said pressure sensor means including means within said housing for reciprocally actuating said piston in response to a change of pressure within said other of said chambers due to a change of pressure within said inhale/exhale breathing conduit, said pressure sensor means having valve chambers in alternating fluid flow communication with said means for varying volume of said breathing storage chamber whereby pressure of inhalation/exhalation drives said means for varying pressure of said breathing storage chamber to increase/decrease pressure, respectively, of said breathing storage chamber.

2. The rebreathing apparatus as defined by claim 1 wherein said breathing storage chamber includes a top wall, bottom wall and bellowed side walls, said bottom wall moves relative to said top wall for varying pressure of said breathing storage chamber.

3. The rebreathing apparatus as defined by claim 2 wherein a breathing gas cylinder and piston are associated with said breathing storage chamber, said piston including a rod member connected to said bottom wall for moving said bottom wall relative to said top wall.

4. The rebreathing apparatus as defined by claim 2 or 3 wherein said piston in said breathing gas cylinder defines an upper chamber and a lower chamber one of said chambers of said breathing gas cylinder being in fluid flow communication with said valve chamber of said pressure sensor means in constant fluid communication with ambient pressure and another of said chambers of said breathing gas cylinder being in fluid flow communication with said valve chambers of said pressure sensor means in fluid communication with said inhale/exhale breathing conduit.

5. The rebreathing apparatus as defined by claim 4 wherein said one of said cylinder of said breathing gas chamber is said upper chamber thereof and wherein said another of said chambers of said breathing gas cylinder is said lower chamber thereof.

6. The rebreathing apparatus as defined by claim 5 and further including a first conduit member for providing fluid communication between said upper chamber of said breathing gas cylinder and said valve chamber of said pressure sensor associated with said chamber in fluid communication with ambient pressure and a second conduit member for providing fluid communication between said lower chamber of said breathing gas cylinder and said valve chamber of said pressure sensor associated with said chamber in fluid communication with said inhale/exhale breathing conduit and further including a third conduit member in fluid flow with said conduit means of said breathing gas supply tank, said third conduit including orifice members between said conduit means and said first and second conduit members.

7. The rebreathing apparatus as defined by claim 4 wherein said valve chambers of said pressure sensor means are sealed by a flexible membrane with respect to said associated chambers of said pressure sensor means.

8. The rebreathing apparatus as defined by claim 6 and further including a spring member for biasing said piston of said pressure sensor means to create positive pressure in said breathing circuit.

9. The rebreathing apparatus as defined by claim 4 when said spring member is biased to a positive pressure of about 20 mm. of water.

* * * * *

UNITED STATES PATENT AND TRADEMARK OFFICE

CERTIFICATE OF CORRECTION

PATENT NO. : 4,928,685

DATED : May 29, 1990

INVENTOR(S) : ROBERT E. GRAY

It is certified that error appears in the above-identified patent and that said Letters Patent is hereby corrected as shown below:

Column 6:

Claim 5, line 15, "cylinder", should read --chambers --; and line 16, "chamber", should read -- cylinder --.

Column 1, line 6, "(1) Field of the Invention", should be on the following line alone.

Column 1, line 14, "(2) Description of the Prior Art", should be on the following line alone.

Signed and Sealed this

Seventh Day of January, 1992

*Attest:*

HARRY F. MANBECK, JR.

*Attesting Officer* *Commissioner of Patents and Trademarks*